(12) United States Patent
Miyazaki et al.

(10) Patent No.: US 6,830,669 B2
(45) Date of Patent: Dec. 14, 2004

(54) BIOSENSOR

(75) Inventors: Shoji Miyazaki, Ehime (JP); Haruhiro Tsutsumi, Ehime (JP); Eriko Yamanishi, Ehime (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 469 days.

(21) Appl. No.: 09/890,761

(22) PCT Filed: Dec. 1, 2000

(86) PCT No.: PCT/JP00/08508

§ 371 (c)(1),
(2), (4) Date: Oct. 16, 2001

(87) PCT Pub. No.: WO01/40788

PCT Pub. Date: Jun. 7, 2001

(65) Prior Publication Data

US 2004/0016642 A1 Jan. 29, 2004

(30) Foreign Application Priority Data

Dec. 3, 1999 (JP) .......................................... 11-344495

(51) Int. Cl.⁷ .............................................. G01N 27/26
(52) U.S. Cl. ................. 204/409; 204/416; 204/403.14; 204/403.01
(58) Field of Search ...................... 204/403.01, 403.14, 204/404, 405, 409, 416; 422/50, 52, 55–59, 61, 68.1

(56) References Cited

U.S. PATENT DOCUMENTS

| | | | |
|---|---|---|---|
| 4,849,340 A | * 7/1989 | Oberhardt | .................. 435/13 |
| 4,929,330 A | * 5/1990 | Osaka et al. | ........... 204/403.05 |
| 4,929,426 A | 5/1990 | Bodai et al. | .................. 422/63 |
| 5,120,420 A | 6/1992 | Nankai et al. | .......... 204/403.11 |
| 5,437,999 A | 8/1995 | Diebold et al. | ......... 204/403.11 |
| 5,759,364 A | * 6/1998 | Charlton et al. | ....... 204/403.14 |
| 5,798,031 A | * 8/1998 | Charlton et al. | ....... 204/403.14 |
| 6,261,519 B1 | * 7/2001 | Harding et al. | ............... 422/58 |
| 6,270,637 B1 | * 8/2001 | Crismore et al. | ...... 204/403.04 |
| 6,287,451 B1 | * 9/2001 | Winarta et al. | .......... 205/777.5 |
| 6,303,081 B1 | * 10/2001 | Mink et al. | .................... 422/61 |

FOREIGN PATENT DOCUMENTS

| | | | |
|---|---|---|---|
| AU | 6378398 | 11/1998 | |
| EP | 0321736 A2 | * 6/1989 | .......... G01N/33/53 |
| EP | 877244 | 11/1998 | .......... G01N/27/327 |
| EP | 1152239 A1 | 11/2001 | .......... G01N/27/327 |
| JP | 52-139778 | * 11/1977 | ............. C07G/7/02 |
| JP | 59-57156 | * 2/1984 | .......... G01N/27/30 |
| JP | 08-185999 | 7/1996 | ............. H05H/1/52 |
| JP | 10-318970 | 12/1998 | .......... G01N/27/327 |
| NO | 981684 | 11/1998 | |
| WO | 99/30152 | 6/1999 | .......... G01N/33/48 |
| ZA | 9803200 | 11/1998 | |

OTHER PUBLICATIONS

Derwent abstract of Tateishi Electronics (JP 52–139778).*
JPO abstract of Katayama et al. (JP 59–57156).*
Patent Abstracts of Japan, vol. 1996, No. 09, Sep. 30, 1996 & JP 08 131791 A (UBE Ind Ltd), May 28, 1996.

* cited by examiner

*Primary Examiner*—Alex Noguerola
(74) *Attorney, Agent, or Firm*—Wenderoth, Lind & Ponack, L.L.P.

(57) ABSTRACT

A biosensor having an electrode layer, which includes a working electrode and a counter electrode, and a reagent layer 10 are formed on an insulating support. Further, a spacer having a long and narrow cut-out portion on the reagent layer is bonded to a cover having an air hole to form a cavity that sucks blood as a liquid sample by capillary phenomenon, and a portion of side walls of the spacer and the cover, which side walls face the cavity, is subjected to a treatment for making the portion itself have hydrophilicity. Accordingly, when blood is sucked into the cavity by capillary phenomenon, the suction is promoted, and the performance of a sensor of the biosensor is improved. Further, the process of manufacturing the sensor is simplified, thereby resulting in increased productivity.

13 Claims, 3 Drawing Sheets

BIOSENSOR

This application is the National Stage, under 35 U.S.C. § 371, of International Application No. PCT/JP00/08508, filed on Dec. 1, 2000 and amended Aug. 3, 2001.

TECHNICAL FIELD

The present invention relates to a biosensor for analyzing a specific component in a liquid sample and, more particularly, to a biosensor having a cavity into which a liquid sample is drawn by capillary phenomenon.

BACKGROUND ART

As a biosensor for analyzing a specific component in a liquid sample, there is, for example, a biosensor for detecting a blood sugar level or the like by measuring a current value that is obtained by a reaction between glucose in blood and a reagent such as glucose oxidase or the like which is held in the sensor.

FIG. 4 is an exploded perspective view illustrating a conventional biosensor for measuring a blood sugar level as described above.

In FIG. 4, a working electrode 1 and a counter electrode 2 are formed by printing on an insulating support 5 comprising polyethylene terephthalate or the like, a reagent layer 10 including glucose oxidase and an electron acceptor is formed on the working and counter electrodes 1 and 2 and, further, a surfactant layer 11 comprising yolk lecithin or the like is formed on the reagent layer 10.

Furthermore, on the surfactant layer 11, a spacer 7 having a long and narrow cut-out portion on the electrodes and the reagent layer 10, and a cover 6 having an air hole are bonded together onto the insulating support 5 so as to form a cavity 12 in which a specific amount of sampled blood is made to react with the reagent layer 10, and a current value that is generated by such a reaction is detected with the working and counter electrodes 1 and 2.

In the biosensor constructed as described above, blood is drawn from a suction inlet 8 into the cavity 12 by capillary phenomenon, and is guided to the position where the electrodes and the reagent layer 10 are presently located. Then, a current value that is generated by a reaction between the blood and the reagent on the electrodes is read by an external measuring apparatus (not shown) that is connected to the biosensor through leads 3 and 4, and a blood sugar level in the blood is obtained according to the current value.

Conventionally, when blood is applied onto the suction inlet 8 and sampled, in order to draw the blood quickly and deep into the cavity 12 by capillary phenomenon, it has been proposed that the surfactant layer 11 is spread so as to cover the reagent layer 10.

However, in the conventional biosensor which facilitates the drawing of blood into the cavity 12 by providing the surfactant layer 11 over the reagent layer 10, since the blood is drawn into the cavity 12 while dissolving the surfactant layer 11 and, further, since the blood reacts with the reagent layer 10 on the electrodes 1 and 2 while dissolving the reagent layer 10, the surfactant layer 11 prevents the reagent layer 10 from dissolving into the blood, and this causes variations in the sensitivity of the sensor or in the measured value, thereby resulting in a detrimental effect on the performance of the sensor.

Further, in the construction of the conventional biosensor, after the reagent layer 10 is formed by spreading a solution including glucose oxidase and an electron acceptor over the electrodes and then drying the solution, the formation of the surfactant layer 11 on the reagent layer 10 requires a step of applying and spreading a solution including a surfactant so as to cover the reagent layer 10, and a step of drying the surfactant layer. Therefore, the process of manufacturing the biosensor takes a much greater time, which results in poor productivity.

The present invention is made to solve the above-described problems. An object of the present invention is to provide a biosensor which can promote the flow of blood into the cavity so as to quickly and sufficiently draw the blood into the cavity without forming a surfactant layer on the reagent layer.

SUMMARY OF THE INVENTION

According to a first aspect of the present invention, in a biosensor which is provided with a cavity into which a liquid sample is drawn by capillary phenomenon and which is able to analyze a component in the liquid sample by a reaction between the drawn liquid sample and a reagent, the surface itself of at least a portion of side walls of the sensor facing the cavity has hydrophilicity.

According to the biosensor constructed as described above, since at least a portion of the side walls of the sensor, which side walls face the cavity into which the liquid sample is drawn by capillary phenomenon, has hydrophilicity at its surface, suction of the liquid sample can be promoted without providing a surfactant layer on the reagent that reacts with the liquid sample. Accordingly, the process of manufacturing the sensor can be simplified.

According to a second aspect of the present invention, in accordance with the biosensor of the first aspect, the side walls of the sensor facing the cavity are made of a resin material in which a surfactant is mixed.

According to the biosensor constructed as described above, since the side walls having hydrophilicity are made of a resin material in which a surfactant is mixed, suction of the liquid sample can be promoted without providing a surfactant layer on the reagent that reacts with the liquid sample, and the process of manufacturing the sensor can be simplified.

According to a third aspect of the present invention, in accordance with the biosensor of the second aspect, the amount of the surfactant to be mixed is 0.01 weight % or more of the resin material.

According to the biosensor constructed as described above, since the side walls of the sensor facing the cavity are made of a resin material into which a surfactant of 0.01 weight % or more of the resin material is mixed, a sufficient blood suction promoting effect can be achieved.

According to a fourth aspect of the present invention, in accordance with the biosensor of the first aspect, the side walls of the sensor facing the cavity are made of a film whose surface is covered with a surfactant.

According to the biosensor constructed as described above, since the side walls of the sensor having hydrophilicity are made of a film whose surface is covered with a surfactant, suction of the liquid sample can be promoted without providing a surfactant layer on the reagent that reacts with the liquid sample and, accordingly, the process of manufacturing the sensor can be simplified.

According to a fifth aspect of the present invention, in accordance with the biosensor of the first aspect, the side walls of the sensor facing the cavity are made of a film whose surface is covered with a resin having a hydrophilic polar group.

According to the biosensor constructed as described above, since the side walls of the sensor having hydrophilicity are made of a film whose surface is covered with a resin having a hydrophilic polar group, suction of the liquid sample can be promoted without providing a surfactant layer on the reagent that reacts with the liquid sample and, accordingly, the process of manufacturing the sensor can be simplified.

According to a sixth aspect of the present invention, in accordance with the biosensor of the fourth or fifth aspect, the thickness of the surfactant or the resin having a hydrophilic polar group, which covers the film, is several tens of angstroms or more.

According to the biosensor constructed as described above, since the side walls of the sensor facing the cavity are made of a film that is covered with the surfactant or the resin having a hydrophilic polar group, a sufficient blood suction promoting effect can be achieved.

According to a seventh aspect of the present invention, in accordance with the biosensor of the first aspect, the surface of at least a portion of the side walls forming the cavity is chemically reformed.

According to the biosensor constructed as described above, since the surface of at least a portion of the side walls forming the cavity is chemically reformed so as to form the side walls of the sensor having hydrophilicity, suction of the liquid sample can be promoted without providing a surfactant layer on the reagent that reacts with the liquid sample, and accordingly, the process of manufacturing the sensor can be simplified.

According to an eighth aspect of the present invention, in accordance with the biosensor of the seventh aspect, a hydrophilic functional group is formed on the surface of at least a portion of the side walls facing the cavity by subjecting the surface to any of the following treatments: plasma discharge, coupling reaction, ozone treatment, and UV treatment.

According to the biosensor constructed as described above, the surface of at least a portion of the side walls forming the cavity is subjected to any of the following chemical surface treatments: plasma discharge, coupling reaction, ozone treatment, and UV treatment, thereby forming a hydrophilic functional group on the surface. Therefore, the surface of at least a portion of the side walls facing the cavity can have hydrophilicity.

According to a ninth aspect of the present invention, in accordance with the biosensor of the first aspect, the surface of at least a portion of the side walls facing the cavity is made of a rough surface.

According to the biosensor constructed as described above, since the surface of at least a portion of the side walls forming the cavity is roughened so as to form the side walls of the sensor having hydrophilicity, suction of the liquid sample can be promoted without providing a surfactant layer on the reagent that reacts with the liquid sample, and, accordingly, the process of manufacturing the sensor can be simplified.

According to a tenth aspect of the present invention, in accordance with the biosensor of the ninth aspect, a rough surface is formed at the surface of at least a portion of the side walls facing the cavity by subjecting the surface to any of the following treatments: sand blasting, electric discharge, non-glare treatment, mat treatment, and chemical plating.

According to the biosensor constructed as described above, the surface of at least a portion of the side walls forming the cavity is subjected to any of the following treatments: sand blasting, electric discharge, non-glare treatment, mat treatment, and chemical plating, thereby forming a rough surface. Therefore, the surface of at least a portion of the side walls facing the cavity can have hydrophilicity.

According to an eleventh aspect of the present invention, in accordance with the biosensor of any one of the first through tenth aspects, the surface of the support, on which the reagent that reacts with the liquid sample is formed, also has hydrophilicity.

According to the biosensor constructed as described above, not only the surface of at least a portion of the side walls forming the cavity but also the surface of the support on which the reagent that reacts with the liquid sample is formed, have hydrophilicity. Therefore, the area of the portion having hydrophilicity in the side walls facing the cavity is increased, whereby the liquid sample can be drawn with higher efficiency.

According to a twelfth aspect of the present invention, in accordance with the biosensor of any one of the first through tenth aspects, the surface of the support on which electrodes that detect the reaction between the liquid sample and the reagent are formed also has hydrophilicity.

According to the biosensor constructed as described above, not only the surface of at least a portion of the side walls forming the cavity but also the surface of the support on which the electrodes for detecting the reaction between the liquid sample and the reagent are formed have hydrophilicity. Therefore, the adhesion of the electrodes to the support on which the electrodes are formed is improved, and the problem of electrode peeling is solved, whereby the reliability of the sensor is improved.

According to a thirteenth aspect of the present invention, in accordance with the biosensor of the twelfth aspect, the surface of the support is made of a rough surface, and the level of the rough surface to be formed is 0.001 $\mu$m to 1 $\mu$m.

According to the biosensor constructed as described above, since a rough surface having unevenness in a level from 0.001 $\mu$m to 1 $\mu$m is formed at the surface of at least a portion of the side walls of the sensor facing the cavity, the adhesion is improved.

DETAILED DESCRIPTION OF THE INVENTION

First Embodiment

Hereinafter, a first embodiment of the present invention will be described with reference to FIG. 1.

Initially, the construction of a biosensor according to the first embodiment will be described with reference to FIG. 1.

Figure 1:
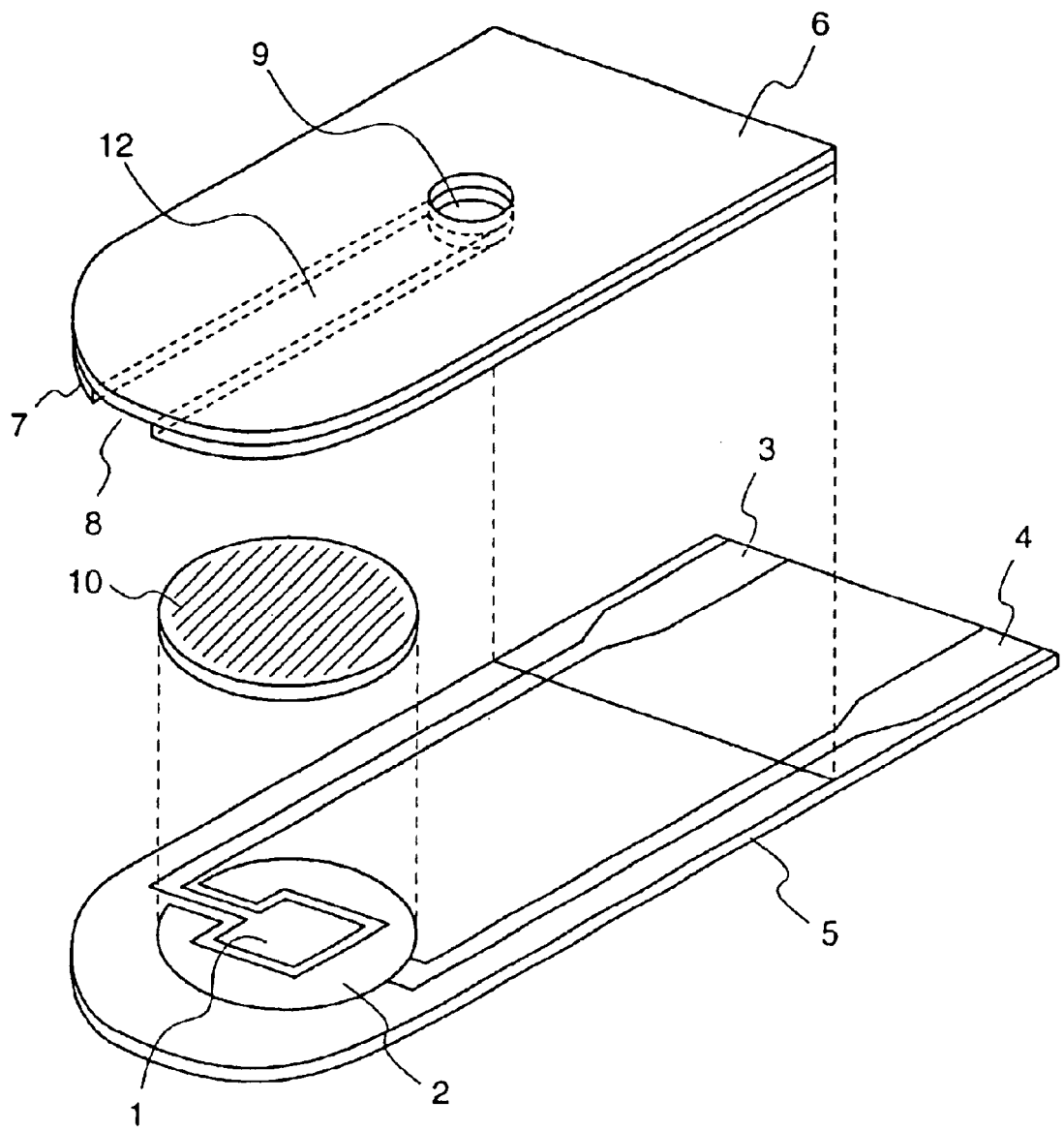
FIG. 1 is an exploded perspective view illustrating a biosensor for measuring a blood sugar level according to embodiments of the present invention.

FIG. 1 is an exploded perspective view of a biosensor according to the first embodiment of the present invention, and this biosensor is different from the conventional biosensor in that the surfactant layer 11 that is formed on the reaction reagent layer 10 of the conventional biosensor is dispensed with. As a substitute for the surfactant layer 11, at least a portion of the side walls facing the cavity 12 into which blood is drawn, i.e., at least a portion of parts of the spacer 7 and the cover 6, which parts face the cavity 12, is made to itself have hydrophilicity so as to promote the drawing of the blood.

Hereinafter, a description will be given of specific methods for making the surfaces of the cover 6 and the spacer 7 facing the cavity 12 to have hydrophilicity.

One of the methods is as follows. An insulating film is formed by mixing a chemical having surface activity such as a surfactant or the like into a material such as polyethylene terephthalate, polycarbonate or the like, and the cover 6 and the spacer 7 are constituted by the insulating film. Thereby, the wettability of the side walls of the cavity 12 is increased, and the blood that is sampled from the suction inlet 8 can be quickly and reliably drawn into the cavity 12.

The kinds of surfactants which can be expected to have the above-mentioned effects when being mixed into the insulating film (classified as hydrophilic groups) are as follows: anionic surfactants such as carboxylate, sulfonate, ester phosphate, and the like; cationic surfactants such as primary amine salt, secondary amine salt, tertiary amine salt, quaternary ammonium salt, and the like; ampholytic surfactants such as amino-acid base surfactants, betaine base surfactants, and the like; and non-ionic surfactants such as polyethylene glycol base surfactants, polyalcohol base surfactants, and the like.

Further, as the materials of the cover 6 and the spacer 7 into which the above-mentioned surfactants can be mixed, there are, besides those already mentioned above, polybutylene terephthalate, polyamide, polyvinyl chloride, polyvinylidene chloride, polyimide, nylon, and the like.

As described above, according to the first embodiment of the present invention, the side walls facing the cavity 12 into which blood is drawn, i.e., the portions of the cover 6 and the spacer 7 facing the cavity 12, are made to have hydrophilicity by mixing a chemical having surface activity such as a surfactant or the like into the material itself of the cover 6 and the spacer 7. Therefore, the wettability of the side walls of the cavity 12 is increased, whereby the blood that is sampled from the suction inlet B can be quickly and reliably drawn into the cavity 12. Accordingly, the surfactant layer 11 of the conventional biosensor on the reagent layer 10 can be dispensed with, and the process of manufacturing the biosensor can be simplified.

The blood suction promoting effect obtained by mixing the surfactant into the insulating base material to be the cover 6 and the spacer 7 is sufficiently recognized when the surfactant of 0.01 weight % or more of the insulating base material is added.

Second Embodiment

Hereinafter, a second embodiment of the present invention will be described with reference to FIG. 1.

Initially, the construction of a biosensor according to the second embodiment will be described with reference to FIG. 1. In the first embodiment, a surfactant is mixed into the material itself of the cover 6 and the spacer 7 so as to make the portions of the cover 6 and the spacer 7 facing the cavity 12 have hydrophilicity. On the other hand, in this second embodiment, any one or more of the surfactants described above for the first embodiment is applied onto an insulating film comprising polyethylene terephthalate, polycarbonate, or the like and made to be a base material of the cover 6 and the spacer 7, or a resin having a hydrophilic polar group at its surface is laminated on the insulating film, so as to coat the insulating film with the surfactant or the resin, thereby making the portions of the cover 6 and the spacer 7 facing the cavity 12 have hydrophilicity.

As the resin having a hydrophilic polar group, there are acrylic resin, polyester resin, urethan resin, and the like.

Further, when forming the hydrophilic coating on the surface of the insulating base material to be the cover 6 and the spacer 7, the base material is not restricted to the above-mentioned insulating film comprising polyethylene terephthalate or polycarbonate, but other materials such as polybutylene terephthalate, polyamide, polyvinyl chloride, polyvinylidene chloride, polyimide, and nylon may be employed.

Furthermore, the hydrophilicity of the side walls of the cavity 12 can be increased so as to enhance the wettability of the side walls by subjecting the surface of the insulating film comprising polyethylene terephthalate, polycarbonate, or the like and to be the base material of the cover 6 and the spacer 7, to primer treatment by using an organotitanium compound, polyethylene imine compound, isocyanate compound, or the like.

As described above, according to the second embodiment, a surfactant is applied onto the insulating film to be the base material of the cover 6 and the spacer 7, or a resin having a hydrophilic polar group at its surface is laminated on the insulating film so as to coat the surfaces of the cover 6 and the spacer 7 with the surfactant or the resin, whereby the side walls facing the cavity 12 into which blood is drawn, i.e., the portions of the cover 6 and the spacer 7 facing the cavity 12, have hydrophilicity. Therefore, the wettability of the side walls of the cavity 12 is increased, whereby the blood that is sampled from the suction inlet 6 can be quickly and reliably drawn into the cavity 12. Accordingly, the surfactant layer 11 of the conventional biosensor on the reagent layer 10 is dispensed with, whereby the process of manufacturing the biosensor can be simplified.

The blood suction promoting effect is recognized when the thickness of the surfactant layer that is applied onto the insulating film as the base material of the cover 6 and the spacer 7 or the thickness of the resin layer having a hydrophilic polar radial to be laminated is several tens of angstroms or more. However, in order to sustain the above-mentioned effect for long hours, the thickness is desired to be several hundreds of angstroms or more.

Third Embodiment

Hereinafter, a third embodiment of the present invention will be described with reference to FIG. 1.

Initially, the construction of a biosensor according to the third embodiment will be described with reference to FIG. 1. In the first embodiment, a surfactant is mixed into the material itself of the cover 6 and the spacer 7 so as to make the portions of the cover 6 and the spacer 7 facing the cavity 12 have hydrophilicity. On the other hand, in this third embodiment, the surfaces of the cover 6 and the spacer 7 facing the cavity 12 are chemically treated or processed so as to make the portions of the cover 6 and the spacer 7 facing the cavity 12 have hydrophilicity.

As specific methods for the chemical surface treatment or the processing on the portions of the cover 6 and the spacer 7 facing the cavity 12, there are, for example, corona discharge and glow discharge which are typical plasma discharge processes.

In such a plasma discharge process, a hydrophilic functional group such as carboxyl group, hydroxyl group, carbonyl group or the like is formed on the surfaces of the cover 6 and the spacer 7 facing the cavity 12, whereby the surface of the material of the cover 6 and the spacer 7 is chemically reformed so as to increase the surface wettability.

Further, as the materials of the cover 6 and the spacer 7 which can be subjected to the above-mentioned chemical treatment, there are polybutylene terephthalate, polyamide, polyvinyl chloride, polyvinylidene chloride, polyimide, nylon, and the like in addition to the above-mentioned polyethylene terephthalate and polycarbonate.

As described above, according to the third embodiment, the surfaces of the cover 6 and the spacer 7 facing the cavity 12 into which the blood is drawn are subjected to the chemical treatment or the processing for chemically reforming the surfaces, whereby the portions of the cover 6 and the spacer 7 facing the cavity 12 have hydrophilicity. Therefore, the wettability of the side walls of the cavity 12 is increased, whereby the blood that is sampled from the suction inlet 8 can be quickly and reliably drawn into the cavity 12. Accordingly, the surfactant layer 11 of the conventional biosensor on the reagent layer 10 is dispensed with, whereby the process of manufacturing the biosensor can be simplified.

Further, as the processes for chemically reforming the surface property, there are, besides plasma discharge, coupling reaction, ozone treatment, ultraviolet treatment, and the like, and any one of these processes may be employed with the same effects as mentioned above.

Fourth Embodiment

Hereinafter, a fourth embodiment of the present invention will be described with reference to FIG. 1.

Initially, the construction of a biosensor according to the fourth embodiment will be described with reference to FIG. 1. In the first embodiment, a surfactant is mixed into the material itself of the cover 6 and the spacer 7 so as to make the portions of the cover 6 and the spacer 7 facing the cavity 12 have hydrophilicity. On the other hand, in this fourth embodiment, the surfaces of the cover 6 and the spacer 7 facing the cavity 12 are roughened so as to form a fine and continuous rough-texture (asperities) on the material surface, thereby making the portions of the cover 6 and the spacer 7 facing the cavity 12 have hydrophilicity.

As specific methods for roughening the surfaces of the cover 6 and the spacer 7, there are sand blasting, electric discharge, non-glare treatment, mat treatment, chemical plating, and the like. The surfaces of the cover 6 and the spacer 7 facing the cavity 12 are roughened by any one of these treatments so as to increase the surface wettability of the cover 6 and the spacer 7.

Further, as the materials of the cover 6 and the spacer 7 on which such treatment can be performed, there are polybutylene terephthalate, polyamide, polyvinyl chloride, polyvinylidene chloride, polyimide, nylon, and the like in addition to the above-mentioned polyethylene terephthalate and polycarbonate.

As described above, according to the fourth embodiment, a fine and continuous rough-texture (asperities) is formed on the surfaces of the cover 6 and the spacer 7 facing the cavity 12 so as to make the portions of the cover 6 and the spacer 7 facing the cavity 12 have hydrophilicity. Therefore, the wettability of the side walls of the cavity 12 is increased, whereby the blood that is sampled from the suction inlet 8 can be quickly and reliably drawn into the cavity 12. Accordingly, the surfactant layer 11 of the conventional biosensor on the reagent layer 10 is dispensed with, whereby the process of manufacturing the biosensor is simplified.

Fifth Embodiment

Hereinafter, a fifth embodiment of the present invention will be described with reference to FIG. 1.

Initially, the construction of a biosensor according to the fifth embodiment will be described with reference to FIG. 1. In the first to fourth embodiments described above, the side walls of the cavity 12, i.e., the portions of the cover 6 and the spacer 7 facing the cavity 12, are processed so as to have hydrophilicity. In this fifth embodiment, not only the cover 6 and spacer 7 but also the surface of the insulating support 5 on which the working electrode 1, the counter electrode 2, and the reagent layer 10 are formed, are subjected to any of the hydrophilic processes described above.

Hereinafter, a description will be given of the effects which are obtained by subjecting, not only the cover 6 and the spacer 7, but also the insulating support 5 to the hydrophilic process.

Initially, as a first effect, when the surface of the insulating support 5 is processed so as to have hydrophilicity, suction of the liquid sample can be further promoted.

For example, in the case where the height of the suction inlet 8 (which is approximately equal to the thickness of the spacer 7) is relatively large (0.3 mm or more in the sensor shown in FIG. 1), when the suction inlet 8 sucks, as a liquid sample, blood having a high hematocrit value under a low-temperature environment (10° C. or lower), the effect of promoting the suction is not satisfactorily obtained by making only the cover 6 and spacer 7 have hydrophilicity as described above, and the suction ability tends to decrease. Therefore, in addition to the cover 6 and the spacer 7, the insulating support 5 is subjected the hydrophilic process as described for any of the first to fourth embodiments, whereby suction of the liquid sample can be further promoted.

Next, as a second effect, when the electrodes are formed on the surface of the insulating support 5 that has been processed so as to have hydrophilicity, the adhesion of the electrodes to the insulating support 5 is dramatically increased.

For example, in manufacturing biosensors, when a biosensor as shown in FIG. 1 is obtained by die-cutting an insulating support 5 with a press or the like according to the outline of the sensor after bonding onto the insulating support 5 on which plural electrodes and reagent layers 10 are formed, a spacer 7 having cut-out grooves for forming cavities 12 in positions corresponding to the respective electrodes and reagent layers, and a cover 6 having air holes 9 in the corresponding positions, the electrodes peel off from the insulating support 5 or the electrodes are cracked due to a shock that occurs when the insulating support 5 is die-cut. This is because the electrodes are formed by printing a paste comprising a conductive material on the insulating support 5, where the polarity of insulating support 5 is inherently very small. Therefore, the insulating support 5 is also subjected to the hydrophilic process as described for any of the first to fourth embodiments to make the material surface of the insulating support 5, the surface of which inherently has a very small polarity, have a polarity, whereby spread and adhesion of the paste which comprises a conductive material and which is used as a material of the electrodes are improved. Therefore, the electrodes are prevented from peeling off from the insulating support 5, or from being cracked.

As described above, according to the fifth embodiment, since not only the cover 6 and the spacer 7 facing the cavity 12 but also the insulating support 5 are subjected to the hydrophilic process, suction of the blood that is sampled from the suction inlet 8 is further promoted as compared with the case where only the cover 6 and the spacer 7 are subjected to the hydrophilic process. Furthermore, since the insulating support 5 is subjected to the hydrophilic process before the formation of the electrodes so as to make the insulating support 5 have a polarity, adhesion of the electrodes to the insulating support 5 is increased, whereby peeling-off of the electrodes from the insulating support 5 and cracking of the electrodes, which have occurred during manufacturing of the biosensor (a blood sugar measuring sensor), are avoided. In the method of roughening the material surface, which is the hydrophilic process described for the fourth embodiment, the level of the rough surface (asperities) at which the effect of adhesion can be expected is within a range of 0.001 $\mu$m-1 $\mu$m, where 0.01 $\mu$m-0.1 $\mu$m are especially desirable.

Hereinafter, first and second examples of the present invention will be described.

EXAMPLE 1

On an insulating support 5 which comprises polyethylene terephthalate and which has been subjected to corona discharge (power: 400 W, rate of discharge: 30 m/min), an electrode layer comprising a working electrode 1 and a counter electrode 2 is formed by screen printing, and a reagent layer 10 including an enzyme (glucose oxidase) and an electron acceptor (potassium ferricyanide) is formed on the electrode layer. Thereafter, a spacer 7 comprising polyethylene terephthalate is bonded to a cover 6 comprising polyethylene terephthalate in which about 1% of alkylbenzene sulfonate, as an anionic surfactant, is blended, thereby fabricating a blood sugar measuring sensor having a groove as a capillary tube into which blood is drawn.

Table 1 shows the blood suction ability of the sensor fabricated in this manner. Here, a suction inlet 8 having a height of 0.17 mm and a width of 2.0 mm is used. Each numeric value in Table 1 indicates a time that is required until the groove, as a capillary tube into which blood is drawn, is completely filled with the blood, under hostile environments (environmental temperature: 5° C. hematocrit: 65%), and the result proves that the same blood suction promoting effect as the blood suction promoting effect that is obtained by the conventional sensor is achieved.

TABLE 1

|  | conventional sensor | sensor of Example 1 |
| --- | --- | --- |
| 1 | 0.54 | 0.68 |
| 2 | 0.69 | 0.58 |
| 3 | 0.69 | 0.72 |
| 4 | 0.63 | 0.65 |
| 5 | 0.72 | 0.64 |
| average (sec) | 0.65 | 0.65 | comparison of blood suction rates (n = 5)

While the indices of wettability (surface tension) of the insulating support 5 and the cover 6 which comprise polyethylene terephthalate used in Example 1 are 48 dyn/cm when they are not processed, the index of the wettability at the surface of the insulating support 5 after being subjected to corona discharge and the index of the wettability at the surface of the cover 6 into which alkylbenzene sulfonate is blended are 54 dyn/cm or more, whereby this result indicates that sufficient wettability for promoting blood suction is secured.

Figure 2:
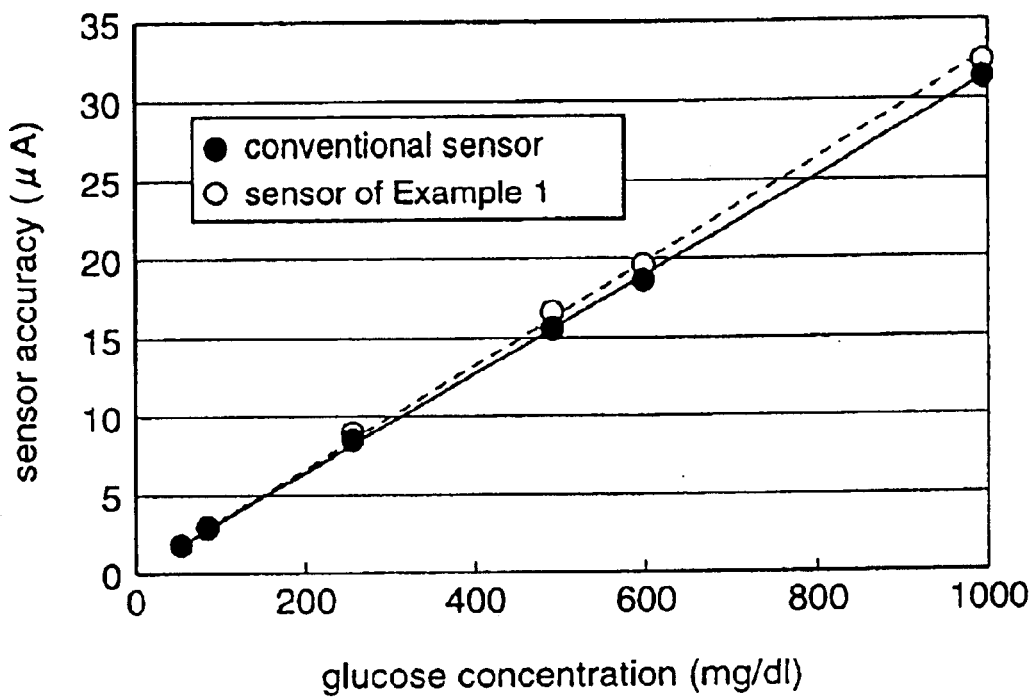
FIG. 2 is a graph showing the result of a comparison of the sensitivities to blood between a sensor according to Example 1 of the present invention and a conventional sensor.

FIG. 2 shows the result of a comparison of the sensor sensitivities at the blood glucose concentrations of 53–992 mg/dl. The sensor sensitivity is detected as follows. After the blood is drawn into the capillary tube, a reaction between the reagent and glucose in the blood is promoted for about 25 seconds, and then, a voltage of 0.5 V is applied between the leads 3 and 4. A current value which is detected five seconds after the voltage application is the sensor sensitivity. Each numerical value in the graph shown in FIG. 2 is an average of n=10 times of measuring. As shown in FIG. 2, the sensitivity of the sensor of Example 1 is about 5% higher than the sensitivity of the conventional sensor. This attests to the result where the non-use of the surfactant layer 11 increases the solubility of the reagent layer 10 that reacts with the blood.

Table 2 shows the result of a comparison of the repetition accuracy (CV values) in the n=10 times of measuring. It can be seen from the result in Table 2 that the measuring variations in the sensor of Example 1 (variations in each sensor) are significantly reduced as compared with the measuring variations in the conventional sensor.

TABLE 2

| glucose concentration | conventional sensor | sensor of Example 1 |
| --- | --- | --- |
| 53 mg/dl | 6.25% | 3.79% |
| 83 mg/dl | 3.15% | 1.67% |
| 253 mg/dl | 3.49% | 1.53% |
| 488 mg/dl | 2.24% | 0.60% |
| 596 mg/dl | 2.49% | 1.86% |
| 992 mg/dl | 2.23% | 2.11% | comparison of sensor accuracy (CV values)

As is evident from the results of FIG. 2 and table 2, a highly-sensitive biosensor with less variations can be realized by employing the sensor of Example 1.

Further, it is also confirmed how much the adhesion between the electrode layer and the insulating support 5 is improved by subjecting the surface of the insulating support 5 to corona discharge. A checker pattern having 100 squares at 1 mm intervals is formed according to JISK5400 (general test method for coating; adhesion; checker-pattern taping method), and the degree of electrode peeling-off is checked with an adhesive cellophane tape. The result is as follows. While peeling-off of electrodes occurs at frequency of 5/100 squares in the conventional sensor performing no corona discharge, it occurs at frequency of 0/100 squares in the sensor of Example 1; that is, a clearly significant difference is confirmed.

EXAMPLE 2

Figure 3:
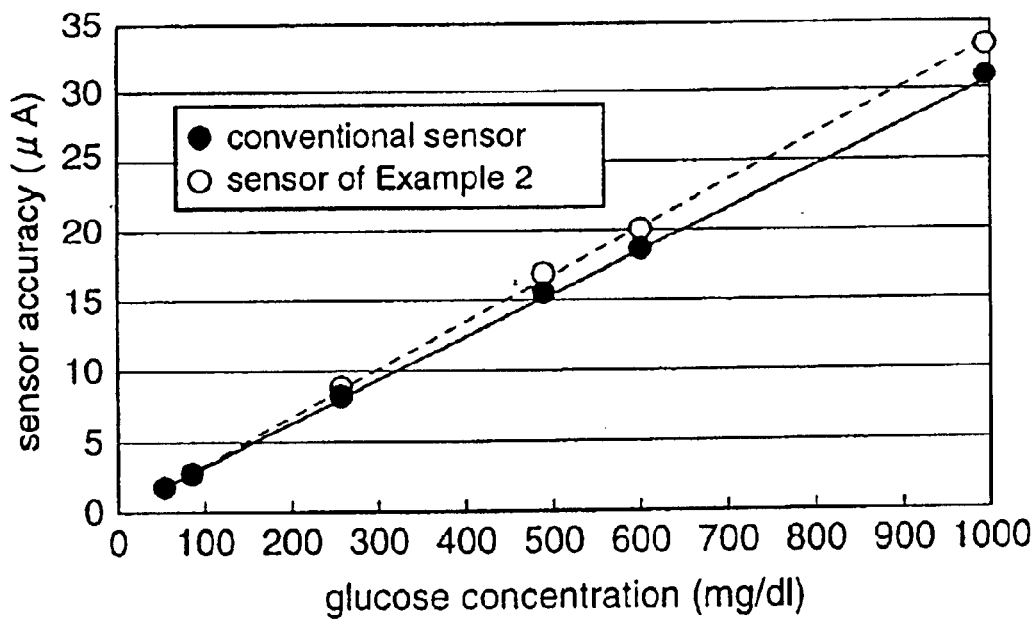
FIG. 3 is a graph showing the result of a comparison of the sensitivities to blood between a sensor according to Example 2 of the present invention and a conventional sensor.
Figure 4:
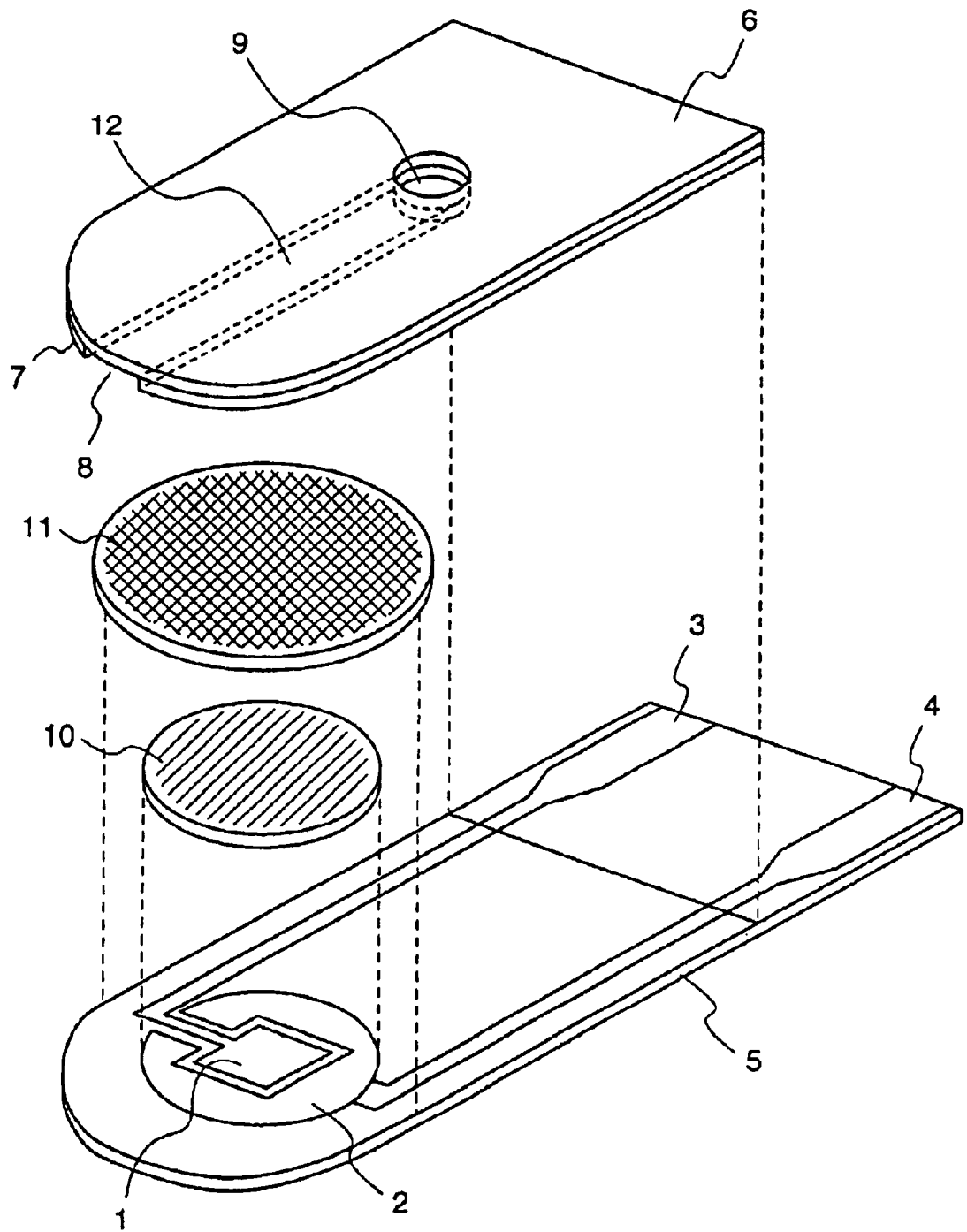
FIG. 4 is an exploded perspective view illustrating a conventional biosensor for measuring a blood sugar level.

On an insulating support 5 comprising polyethylene terephthalate, an electrode layer comprising a working electrode 1 and a counter electrode 2 is formed by screen printing, and a reagent layer 10 including an enzyme (glucose oxidase) and an electron acceptor (potassium ferricyanide) is formed on the electrode layer. Thereafter, a spacer 7 comprising polyethylene terephthalate is bonded to a cover 6 comprising a compound film (the index of surface wettability: 54 dyn/cm or more) which is obtained by laminating a polyester base resin having a hydrophilic polar group on polyethylene terephthalate, thereby fabricating a blood sugar measuring sensor having a groove as a capillary tube into which blood is drawn, and evaluations similar to those of Example 1 are executed. Table 3 shows the result of a comparison of the blood suction rates between the sensor fabricated as described above according the Example 2 and the conventional sensor, FIG. 3 shows the result of a comparison of the sensor sensitivities at the blood glucose concentrations of 53–992 mg/dl, and Table 4 shows the result of a comparison of the repetition sensor accuracy (CV values) in the n=10 times measuring.

TABLE 3

|  | conventional sensor | sensor of Example 2 |
|---|---|---|
| 1 | 0.54 | 0.62 |
| 2 | 0.69 | 0.55 |
| 3 | 0.69 | 0.68 |
| 4 | 0.63 | 0.60 |
| 5 | 0.72 | 0.69 |
| average (sec) | 0.65 | 0.63 | comparison of blood suction rates (n = 5)

TABLE 4

| glucose concentration | conventional sensor | sensor of Example 2 |
|---|---|---|
| 53 mg/dl | 6.25% | 3.88% |
| 83 mg/dl | 3.15% | 2.17% |
| 253 mg/dl | 3.49% | 1.22% |
| 488 mg/dl | 2.24% | 1.60% |
| 596 mg/dl | 2.49% | 1.56% |
| 992 mg/dl | 2.23% | 2.05% | comparison of sensor accuracy (CV values)

From these results, excellent blood suction ability and sensor responsivity (sensitivity, CV value) as high as those of Example 1 are confirmed.

A biosensor according to the present invention is available as a biosensor which improves sensitivity and which reduces variations when analyzing a specific component in a liquid sample that is drawn into a cavity of the sensor by capillary phenomenon.

What is claimed is:

1. A biosensor comprising a cavity into which a liquid sample is drawn by capillary phenomenon, side walls facing the cavity, a support, and electrodes formed on a surface of at least one of said side walls facing the cavity, said electrodes being operable to detect a reaction between the drawn liquid sample and a reagent, and said biosensor being operable to analyze a component in the liquid sample based on the detected reaction, wherein a surface itself of at least a portion of said side walls facing the cavity has hydrophilicity, wherein said side walls facing the cavity are made of a resin material in which a surfactant is mixed by an amount of 0.01 weight % or more of the resin material, wherein the surface of said at least one of said side walls facing the cavity on which said electrodes are formed has hydrophilicity, and wherein a surface of said support is made of a rough surface whose level is 0.001 $\mu$m to 1 $\mu$m.

2. A biosensor comprising a cavity into which a liquid sample is drawn by capillary phenomenon, side walls facing the cavity, a support, and electrodes formed on a surface of at least one of said side walls facing the cavity, said electrodes being operable to detect a reaction between the drawn liquid sample and a reagent, and said biosensor being operable to analyze a component in the liquid sample based on the detected reaction, wherein a surface itself of at least a portion of said side walls facing the cavity has hydrophilicity, wherein said side walls facing the cavity are made of a film whose surface is covered with a surfactant, wherein the surface of said at least one of said side walls facing the cavity on which said electrodes are formed has hydrophilicity, and wherein a surface of said support is made of a rough surface whose level is 0.001 $\mu$m to 1 $\mu$m.

3. A biosensor comprising a cavity into which a liquid sample is drawn by capillary phenomenon, and side walls facing the cavity, said biosensor being operable to analyze a component in the liquid sample by a reaction between the drawn liquid sample and a reagent, wherein a surface itself of at least a portion of said side walls facing the cavity has hydrophilicity, and wherein said side walls facing the cavity are made of a film whose surface is covered with a resin having a hydrophilic polar group.

4. A biosensor according to claim 3, wherein the thickness of the resin having a hydrophilic polar group which covers the film is at least several tens of angstroms.

5. A biosensor according to claim 4, wherein a surface of at least one of said walls on which the reagent that reacts with the drawn liquid sample is formed has hydrophilicity.

6. A biosensor according to claim 4, further comprising electrodes formed on a surface of at least one of said side walls facing the cavity, wherein said electrodes are operable to detect the reaction between the drawn liquid sample and the reagent, and wherein the surface of said at least one of said side walls on which said electrodes are formed has hydrophilicity.

7. A biosensor according to claim 6, further comprising a support, wherein a surface of said support is made of a rough surface whose level is 0.001 $\mu$m to 1 $\mu$m.

8. A biosensor according to claim 3, wherein a surface of at least one of said side walls on which the reagent that reacts with the drawn liquid sample is formed has hydrophilicity.

9. A biosensor according to claim 3, further comprising electrodes formed on a surface of at least one of said side walls facing the cavity, wherein said electrodes are operable to detect the reaction between the drawn liquid sample and the reagent, and wherein the surface of said at least one of said side walls on which said electrodes are formed has hydrophilicity.

10. A biosensor according to claim 9, further comprising a support, wherein a surface of said support is made of a rough surface whose level is 0.001 $\mu$m to 1 $\mu$m.

11. A biosensor comprising a cavity into which a liquid sample is drawn by capillary phenomenon, side walls facing the cavity, a support, and electrodes formed on a surface of at least one of said side walls facing the cavity, said electrodes being operable to detect a reaction between the drawn liquid sample and a reagent, and said biosensor being operable to analyze a component in the liquid sample based on the detected reaction, wherein a surface itself of at least a portion of said side walls facing the cavity has hydrophilicity, wherein a surface of at least a portion of said side walls forming the cavity is chemically reformed, wherein a hydrophilic functional group is formed on a surface of at least a portion of side walls facing the cavity by subjecting the surface on which the hydrophilic functional group is formed to at least one of plasma discharge, coupling reaction, ozone treatment, and UV treatment, wherein the surface of said at least one of said side walls facing the cavity on which said electrodes are formed has hydrophilicity, and wherein a surface of said support is made of a rough surface whose level is 0.001 μm to 1 μm.

12. A biosensor comprising a cavity into which a liquid sample is drawn by capillary phenomenon, side walls facing the cavity, a support, and electrodes formed on a surface of at least one of said side walls facing the cavity, said electrodes being operable to detect a reaction between the drawn liquid sample and a reagent, and said biosensor being operable to analyze a component in the liquid sample based on the detected reaction, wherein a surface itself of at least a portion of said side walls facing the cavity has hydrophilicity, wherein a surface of at least a portion of said side walls forming the cavity is chemically reformed, wherein the surface of said at least one of said side walls facing the cavity on which said electrodes are formed has hydrophilicity, and wherein a surface of said support is made of a rough surface whose level is 0.001 μm to 1 μm.

13. A biosensor comprising a cavity into which a liquid sample is drawn by capillary phenomenon, side walls facing the cavity, a support, and electrodes formed on a surface of at least one of said side walls facing the cavity, said electrodes being operable to detect a reaction between the drawn liquid sample and a reagent, and said biosensor being operable to analyze a component in the liquid sample based on the detected reaction, wherein a surface itself of at least a portion of said side walls facing the cavity has hydrophilicity, wherein the surface of said at least one of said side walls facing the cavity on which said electrodes are formed has hydrophilicity, and wherein a surface of said support is made of a rough surface whose level is 0.001 μm to 1 μm.

* * * * *